United States Patent [19]

Curran

[11] Patent Number: 4,882,677

[45] Date of Patent: Nov. 21, 1989

[54] ISOMETRIC STRENGTH TESTING METHOD AND EQUIPMENT FOR DISABILITY EVALUATION

[76] Inventor: Thomas M. Curran, 464 Springbrook, Saline, Mich. 48176

[21] Appl. No.: 92,432

[22] Filed: Sep. 3, 1987

[51] Int. Cl.[4] .......................... A61B 5/10; A61B 5/22
[52] U.S. Cl. .......................... 364/413.02; 364/551.01; 128/782; 73/379
[58] Field of Search .......................... 128/782; 73/379; 364/413, 415, 551, 413.27, 413.02, 551.01; 358/107

[56] References Cited

U.S. PATENT DOCUMENTS

| | | | |
|---|---|---|---|
| 4,375,674 | 3/1983 | Thornton | 364/413 X |
| 4,631,676 | 12/1986 | Pugh | 364/413 |
| 4,655,227 | 4/1987 | Gracovetsky | 128/782 X |
| 4,664,130 | 5/1987 | Gracovetsky | 128/781 |
| 4,702,108 | 10/1987 | Amundsen et al. | 73/379 |

OTHER PUBLICATIONS

Chaffin, D. B. et al. "Occupational Biomechanics", John Wylie & Sons, Inc., 1984, 53–77, 147–203.
Garg, A. et al "A Biomechanical Computerized Simulation of Human Strength", AIIE Transactions, vol. 7, Mar. 1975, 1–15.
Ghosh, A. K. et al. "Preliminary Study on Static Weight Distribution Under the Human Foot as a Measure of Lower Extremity Disability", Med. & Biol. Eng. & Comput., vol. 17, Nov. 1979, 737–741.
"Work Practices Guide to Manual Lifting", U.S. Dept. of Commerce, NTIS TB82-178948, Mar. 1981, 21.

Primary Examiner—Clark A. Jablon
Attorney, Agent, or Firm—James M. Deimen

[57] ABSTRACT

New disability testing and evaluation software combined with an isometric strength testing machine provides a very complete and standardized means of determining disability in comparison with the norms of the general population. The software utilizes not only the machine but also the digitization of photographs taken of the subject person during each strength test. Combining the digitized photographic data, the force monitor information from the load cell of the machine and extensive anthropomorphic data the software calculates for loading of the weakest joint in the subject person and compares this loading to normative values from the general population. In this manner a percentage disability for a subject person can be calculated with reasonable assurance of the validity and reproducibility of the result. New specialized hand grips for an isometric strength testing machine are disclosed to test grip strength and torsional strength of the hand.

12 Claims, 7 Drawing Sheets

ISOMETRIC STRENGTH TESTING METHOD AND EQUIPMENT FOR DISABILITY EVALUATION

BACKGROUND OF THE INVENTION

The field of the invention pertains to biomechanical strength testing of individual persons and, in particular, to the careful isometric strength testing of individuals disabled as a result of injuries. Strength testing relates to disability evaluations, pre-employment examination, job redesign and work conditioning.

In recent years, the importance of careful biomechanical modeling and the repeatability of results from strength testing to assure validity of the results has taken on great importance to assure that the physical labor required in a job is properly matched with the individual worker. More importantly, avoidance of injury and the proper evaluation of disabling injuries has become important not only because of the cost to the disabled but also the cost to society that also results.

Extensive research and careful analysis of the human body structure under physical stress is disclosed and summarized in a recent book by Don B. Chaffin, Ph.D. and Gunnar Andersson, M.D. entitled, "Occupational Biomechanics", 1984 John Wylie & Sons, Inc. The book presents extensive biomechanical guidelines and considerations for the physical work and workplace of an individual. On the bases of these guidelines and considerations, limits are suggested for various physical activities in various workplace situations.

A publication by the U.S. Department of Commerce, National Technical Information Service, sponsored by the U.S. Department of Health and Human Services, is entitled, "Work Practices Guide for Manual Lifting" and was published in March of 1981 with reference number TB 82-178948. This technical report summarizes research on the hazards of manual materials handling in industry and recommends means to reduce the human and economic burden imposed by improper materials handling. Such recommendations include the safe load, weight, size, location and frequency of handling by a worker. Worker training and selection criteria are listed and engineering guidelines are provided for the design of the workplace.

At the University of Michigan in Ann Arbor, Mich., an isometric strength testing machine was developed with an electric sensor or load cell employed to sense the load applied to the machine by the subject individual. The purpose of the machine is for job analysis and employment screening and the electric sensor is directly connected to interface means to directly record the load applied to the machine by the subject. The machine and considerable supporting mainframe computer software was developed under a National Aeronautics and Space Administration supported contract. The principal publication arising from the research is Garg, A. and Chaffin, D. B., The Human Strength Simulations, Biomechanical Division NASA/MSC Contract #NAS9-10973, April 1972.

The machine comprises a vertical assembly post and a horizontal platform. At various heights on the vertical assembly post, a horizontal arm may be positioned. The horizontal arm contains the necessary sensor and a single or double hand grip for the subject to apply a load to the machine. Depending on the height of the hand grip, the subject may be in various postures, such as partially bent over to lift a load from the platform, pushing against the hand grip, or raising a load over the subject's head. As a result of the development of the machine and the mainframe software, considerable research was accomplished in job analysis and employment screening.

SUMMARY OF THE INVENTION

The invention comprises new specialized hand grips for the testing machine and new software combined with the machine specifically directed toward disability evaluation of subjects. The disability evaluation software utilizes not only the testing machine but also the digitization of photographs of the subject taken in each isometric position as the subject is performing the load test on the machine. The new software combines the digitized information taken from the photographs and the information from the load cell or sensor of the machine along with other information about the subject. The software calculates from this information a number of body dimensions and angles, certain loads and weights that are critical to disability evaluation and the percentage capabilities of various body joints relative to the capability of a large percentage of the general population. The new combination of software and hardware allows the technician to evaluate a subject by having the subject perform the simulated lifting of a load from the platform by isometrically attempting to lift the load over three separate five second intervals. The photographs are taken as the subject is exerting maximum force on the hand grip of the machine. At the same time, the load on the machine is being recorded on a strip chart which typically results in a somewhat bell-shaped curve over each five second time period. The data from the photographs and the strip chart recorder may then be immediately digitized and processed by the disability software or processed subsequently.

For the lifting of a load from the platform, a "tote pan" simple hand grip on the testing machine may be used. The hand grip may be raised to higher positions including an overhead position on the machine. However, two new specialized hand grips have been developed for use in combination with the machine. The first of the new grips provides a simple hand squeezing motion wherein the squeezing motion is strictly limited to sliding motion of the grip. A purely tensile load is placed on the grip by the hand and the grip is insensitive to right-side-up or upside-down placement of the hand. The other new grip comprises a torque sensing attachment. The torque sensing attachment, depending on hand placement and movement, senses flexion/extension torque, pronation/supination torque, and ulnar/radial deviation torque. With each test, the instantaneous load sensed by the testing unit is printed out on a strip chart recorder and the test repeated.

One of the important advantages of the new test methods, software analysis and specialized hand grips is that with repeated testing such as three repeated tests for each load position prescribed, a very confident prediction of the percent disability of the subject in comparison with statistical norms developed from the general population results. Any attempted malingering by the subject also faults the test or appears clearly in the test results.

DESCRIPTION OF THE PREFERRED EMBODIMENTS

Figure 1:
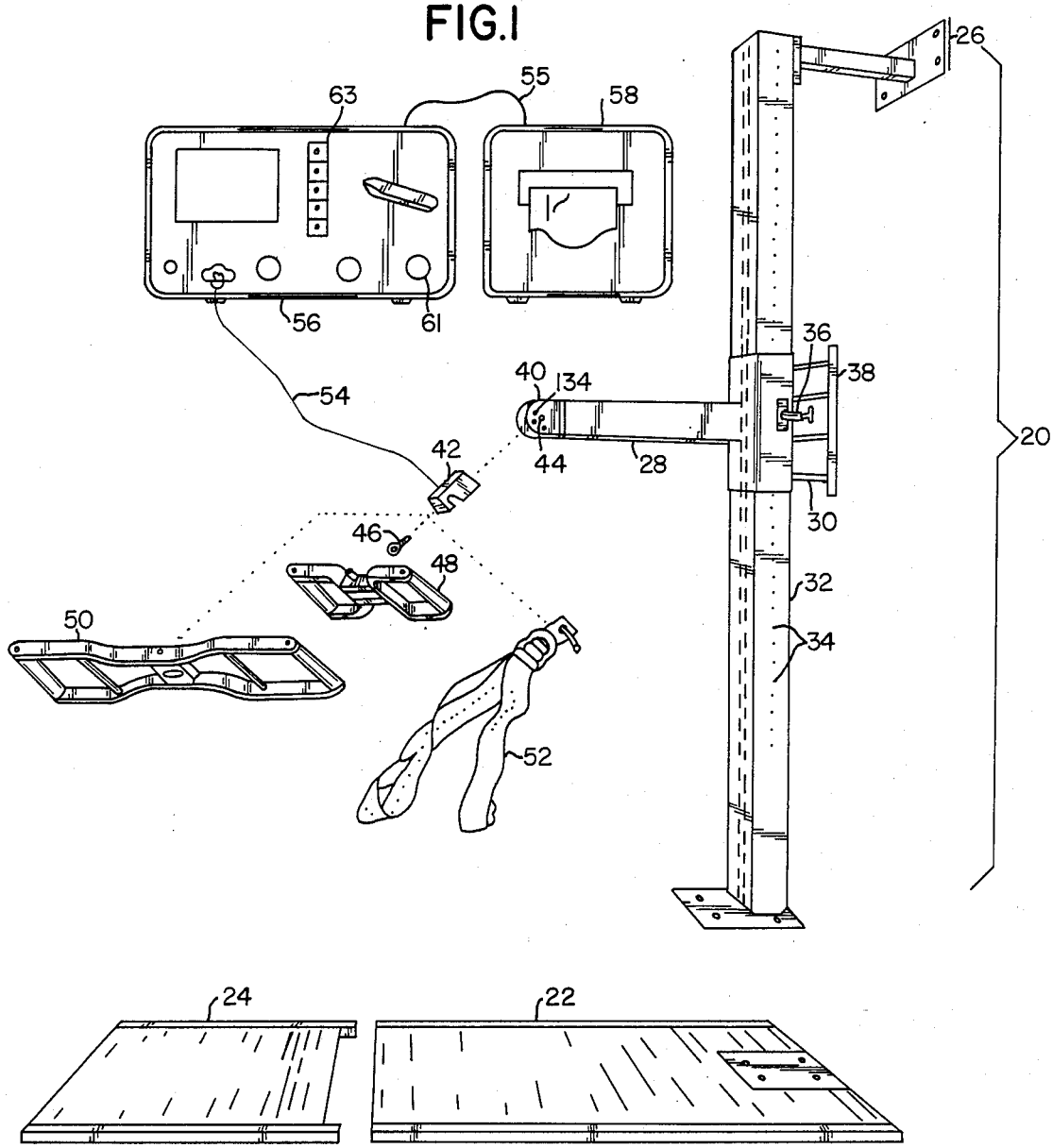
FIG. 1 illustrates an exploded view of the basic platform and vertical assembly plus electronics of the testing machine.

Illustrated in FIG. 1, in exploded view, is a vertical post assembly 20 that attaches to a platform 22 having an extension 24. Atop the vertical post assembly is an optional bracket 26 to attach the post to a wall if the platform is not used. Movable vertically to selectable positions is a horizontal arm 28 having a sleeve 30 about the post 32. The post 32 is provided with holes 34 engageable by a pin 36 with which to select and retain the vertical position desired. The sleeve 30 is also equipped with means 38 movable to squeeze the sleeve tightly to the post and thereby reduce compliance. The horizontal arm 28 is equipped with a head 40 having a load cell 42 that may be rotatably positioned in five separate angular locations relative to the arm 28 about the pivot point 44.

Selectively attachable to the load cell 42 by means of an eye-bolt 46 are a small double handle 48, a large double handle 50 and a parachute strap 52. A subject person standing on the platform 22 may present a variety of isometric loads to the machine depending upon the vertical position of the arm 28, the angular position of the load cell 42 and the particular handle or other attachment to the load cell. For example, the arm may be placed at approximately the hip height of the subject and the parachute strap 52 attached about the hips of the subject. With the subject straining away from the arm 28, an isometric load may be placed on the load cell 42 to simulate the towing or dragging of a load with a strap. Or, the small set of handles 48 attached to the load cell 42 and the arm 28 at approximately chest height of the subject can be used to simulate the pushing of a large load. As a further example, the arm 28 may be positioned at approximately knee height or below with the large handle 50 attached to the load cell 42 and the load cell 42 in the upward vertical position. This configuration simulates the initial lifting load of a tote pan or other similar object. Electrically connected 54 to the load cell 42 is a force monitor 56. In turn electrically connected 55 to the force monitor 56 is a strip chart recorder 58. The force monitor 56 includes test and reset positions on a selectable switch 61 to assure that once the individual test of the subject begins, the subject applies the load to the full extent of his ability for the full five second test period in the examples given below without interruption. Simultaneously, the strip chart recorder 58 plots the load versus time. The test position of the force monitor includes a threshhold setting. If the test subject lets up during the last three seconds of the five second test, a red light 63 signals and the test is voided.

Figure 11:
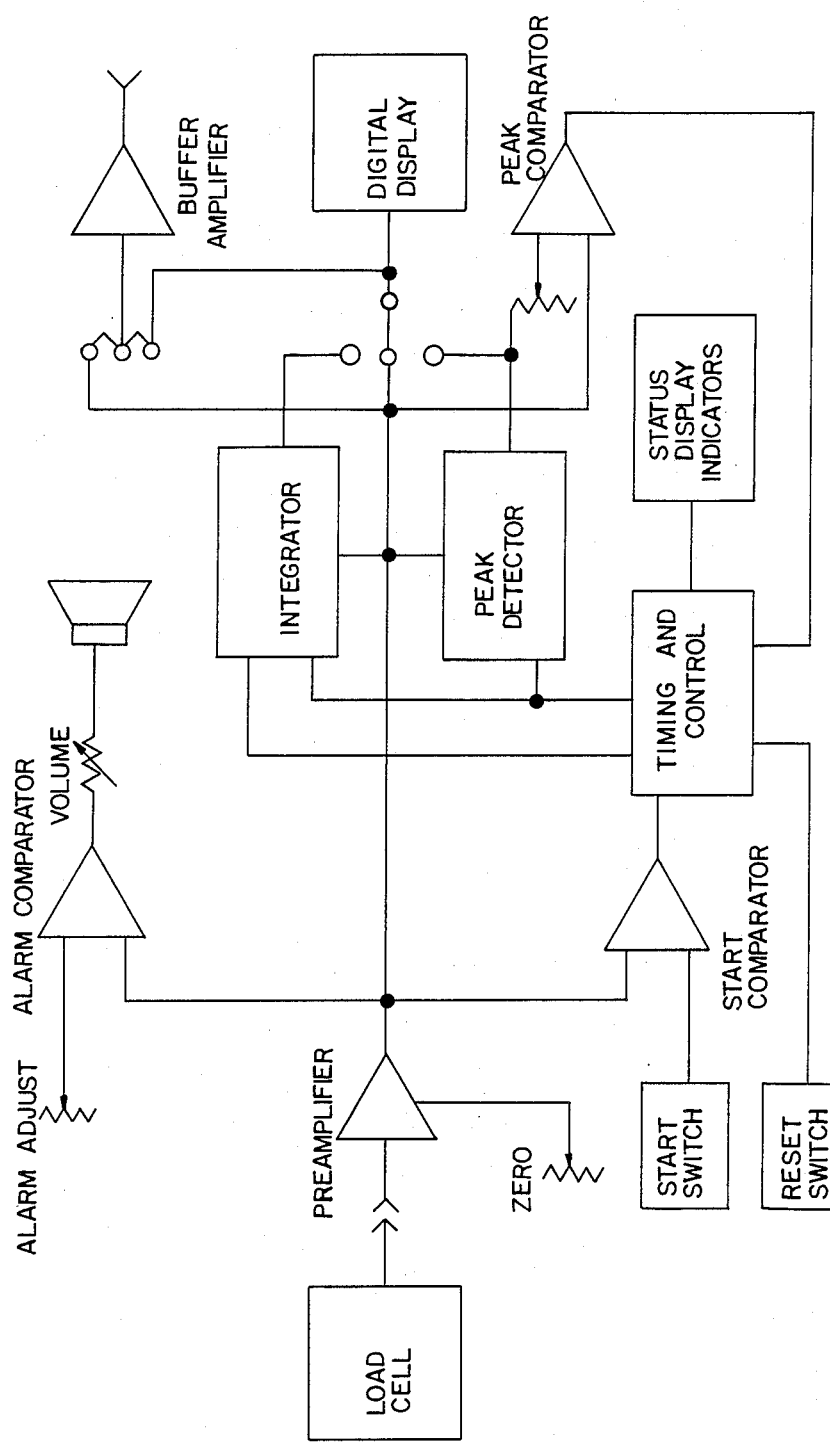
FIG. 11 is a detailed block diagram of the force monitor.

A suitable strip chart recorder 58 is the unit from BBC Metrawatt, Bloomfield, Colo. The force monitor 56 is a signal conditioning and digital display unit for analysis of the forces applied to the load cell 42. The force monitor 56 includes a load cell exitation source, tracking peak detector, gated averaging circuitry, timing and error detecting circuits. Although separate electronic devices can be combined to provide these functions, the force monitor provides an easy to use single unit that can be quickly reset for each test and gives both an audible and visual error signal if a force above a selectable threshhold is not maintained for the full test period. A detailed block diagram of the force monitor 56 is illustrated in FIG. 11.

A basic overall evaluation of a subject person can be obtained by analysis of the results of three isometric tests with the 6 inch handles 48 or 18 inch handles 50. Each test comprises a lift simulation with the arm 28 at the appropriate height on the vertical post 32. For the arm lift the elbows are close to the body and at right angles. Thus, the arm 28 is adjusted in accordance with the stature of the person. For the torso lift and leg lift the vertical height of the hand grips on the handle 50 is 15 inches. For the torso lift the person is placed with the upright torso horizontally 10 inches from the centers of the hands on the handle 50 and for the leg lift the upright torso is even horizontally with the centers of the hands on the handle 48.

Each test is repeated three times to assure repeatibility and the following measurements recorded:

(a) body stature and type of lift.

(b) body angles measured from photographs taken from the side during maximum effort.

(c) average peak forces and peak forces.

(d) force curves.

A comparison is then made against statistical norms derived from the biomechanical modelling in the references noted above. In the disability setting a disability is considered less than 75% performance in comparison to normative maximum values of what a healthy person can accomplish. For the average healthy person 40% of the normative maximum value is considered the repetitive maximum for work in an 8 hour day. For repetitive all day manual lifting the limits considered are 35 lbs. for the average male and 20 lbs. for the average female.

The new disability testing software is specifically directed to analysis of the isometric strength of a subject person engaged in a single task. The task comprises attempting to lift a "tote bin" from the floor and is simulated by positioning the large 18 inch double handle 50 on the head 40 of the arm 28 such that the hand grips are horizontal. The load cell 42 is thus vertical in the head 40. For the test the arm 28 is positioned vertically on the post 32 to place the hand centers 15 inches above the platfor. The subject person is placed with the upright torso about 10 inches horizontally from the centers of the hands.

Figure 2:
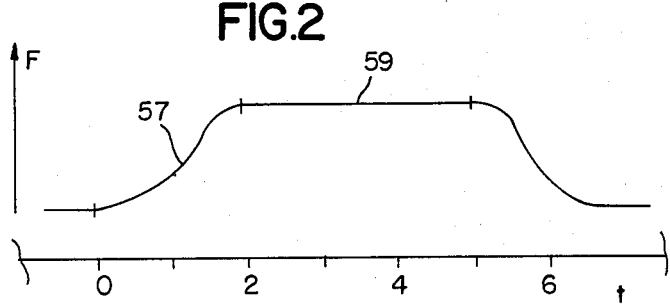
FIG. 2 is a force versus time graph of a test.

The subject person is requested to pull upwardly with both hands on the hand grips with maximum effort for a five second interval during which time a picture from the side is taken of the person. The test is repeated three times with a rest interval of at least two minutes in between. The force monitor 56 is reset between each test and the strip chart recorder 58 prints a curve of force versus time for each test. The curve of force versus time is bell shaped as illustrated in FIG. 2 with the rise time 57 typically about two seconds and hold time 59 the remaining three seconds of the five second test. In the event the subject person relaxes or lets up during the three second maximum force period an error light appears on the force monitor 56. A threshhold force is also set on the force monitor 56 prior to initiation of the test. Thus, malingering will be detected.

Figure 3A:
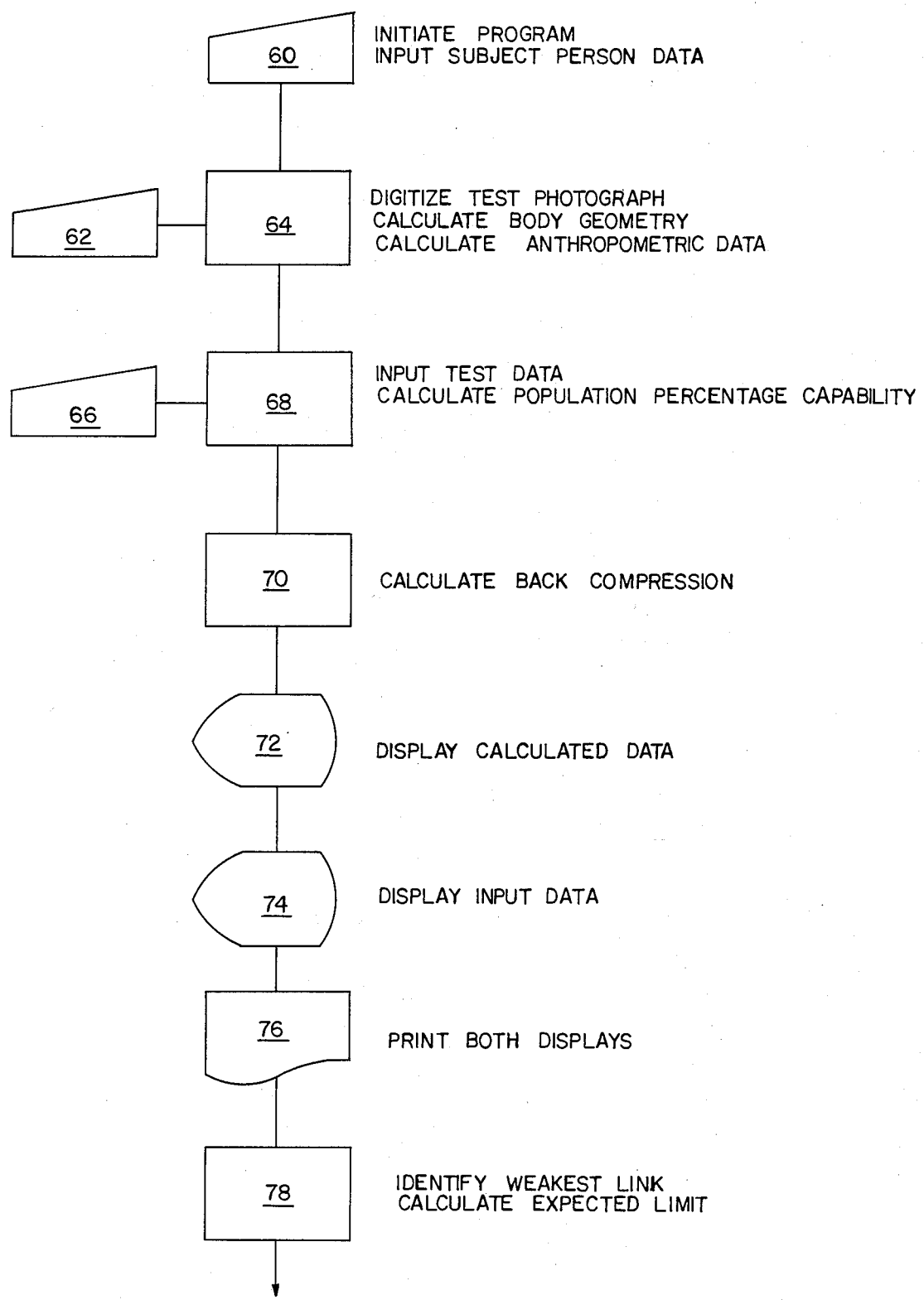
FIGS. 3a and 3b illustrate a biomechanical model flow chart for the software.
Figure 3B:
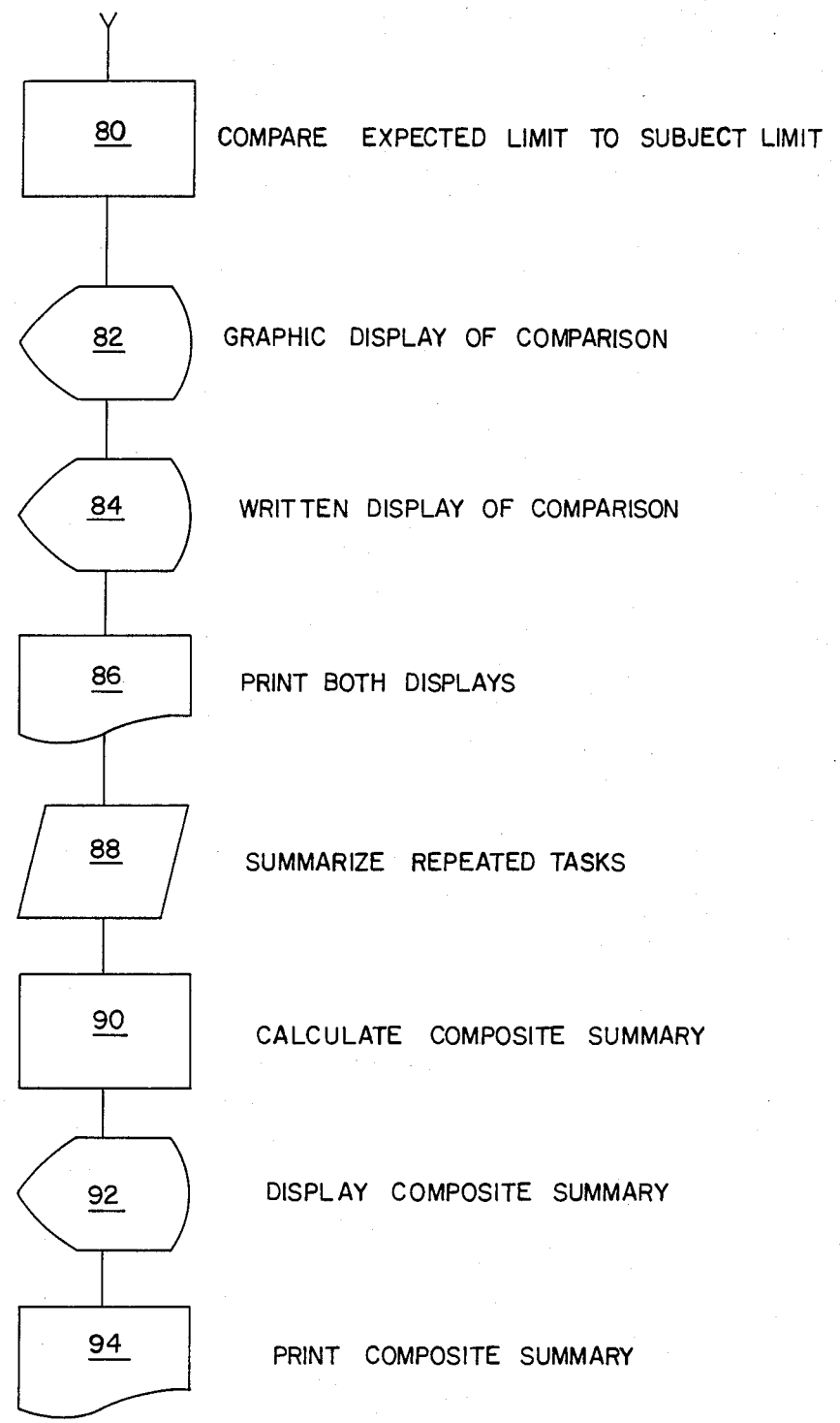

Illustrated in FIGS. 3a and 3b is a biomechanical model flow chart for the software utilized to prepare the "tote bin" isometric test results.

Block 60 denotes the entry of the following subject person data:
English or Metric?
Current date.
Technician.
Subject.
Task #.
Age.
Sex.
Body side (photograph side).
Height.
Weight.

Block 62 denotes digitization of the subject's test photograph and calculation of body geometry including pertinent angles. A Polaroid photograph is suitable with a digitizer from Numonics Corporation, Montgomeryville, Pa.

Block 64 denotes calculation of the anthropometric data using the formulae and approach disclosed in "Occupational Biomechanics", Chapter 3.

Block 66 denotes the entry of the following testing data:
Number of hands.
Direction of motion.
Average peak exertion from force monitor.
Horizontal distance (H).
Vertical distance (V).

Block 68 denotes calculation of the population percentage capability using the approach and formulae disclosed in "Occupational Biomechanics", Chapter 6.

Block 70 denotes calculation of back compression using the formulae and approach in "Occupational Biomechanics", Chapter 6.

Figure 4:
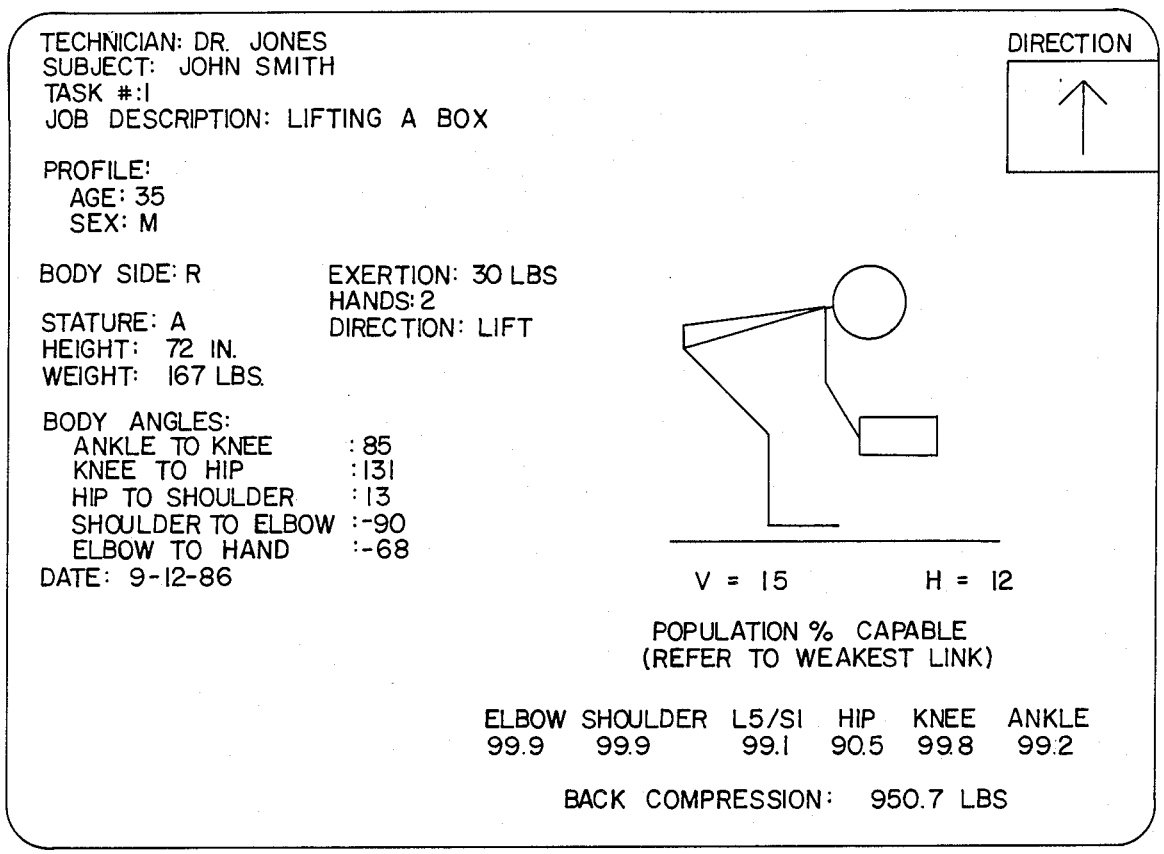
FIG. 4 illustrates an example of the output screen showing the results of the digitization of a photograph and the load calculations.

Blocks 72 and 74 denote screen display of the calculated data and input data entered in the form of a chart as shown in FIG. 4 and a table as follows in a typical example. In the table the figure and page references are to "Occupational Biomechanics".

TABLE 1

Ergometrics Biomechanical Model

Analyst: DR. JONES
Subject: JOHN SMITH                    Age: 35
Task: LIFTING A BOX                    Sex: M

| | |
|---|---|
| Height: | 72 |
| Weight: | 167 |
| Ankle to Knee: | 85 |
| Knee to Hip: | 131 |
| Hip to Shoulder: | 13 |
| Shoulder to Elbow: | −90 |
| Elbow to Hand: | −68 |
| Directon: | 270 |
| Weight: | 30 |
| No. Hands: | 2 |

| | FIG. 3.8, Page 69 | FIG. 3.9, Page 73 | Table 3.11, Page 72 |
|---|---|---|---|
| Body Link | Length (Cm) | Center of Gravity (Cm) | Weight (N) |
| Elbow | 44.99 | 25.51 | 34.15 |
| Shoulder | 44.81 | 25.40 | 77.58 |
| L5/S1 | 9.88 | 4.94 | 141.89 |
| Hip | 40.60 | 36.13 | 269.38 |
| Knee | 34.02 | 14.83 | 23.01 |
| Ankle | 35.48 | 15.26 | 18.93 |

| Calc. From Input Angles | | Page 224 | Page 224 | Page 224 | Page 224 |
|---|---|---|---|---|---|
| Body Link | Included Angle | Flexion | S.D. | Extension | S.D. |
| Elbow | 85.00 | 0.00 | 0.00 | 146.29 | 48.38 |
| Shoulder | 134.00 | 108.43 | 31.81 | 166.35 | 58.27 |
| L5/S1 | 62.00 | 113.00 | 30.84 | 248.34 | 99.73 |
| Hip | 125.21 | 47.85 | 14.06 | 811.79 | 255.88 |
| Knee | 77.00 | 86.74 | 20.05 | 97.62 | 30.58 |
| Ankle | 158.00 | 63.41 | 15.58 | 29.89 | 6.02 |

| | Page 165 Vertical Resultant | | Page 165 Horizontal Resultant | | Total |
|---|---|---|---|---|---|
| Body Link | Force [N] | Moment [NM] | Force [N] | Moment [NM] | Moment [NM] |
| Elbow | −425.98 | −28.02 | −0.00 | 0.00 | −28.02 |
| Shoulder | −391.83 | −11.90 | −0.00 | −0.00 | −11.90 |
| L5/S1 | −314.25 | −117.20 | −0.00 | −0.00 | −117.20 |
| Hip | −486.62 | −205.15 | −0.00 | −0.00 | −205.15 |
| Knee | −108.62 | −9.94 | −0.00 | −0.00 | −9.94 |
| Ankle | −85.61 | −9.94 | −0.00 | −0.00 | −9.94 |

| | | |
|---|---|---|
| Pelvic Angle From Vertical: | 32.1 | Page 192 |
| Angle Alpha From Horizontal: | 17.9 | Page 193 |
| Weight above L5/S1: | 269.4 | Page 72 |
| Diaphragm Moment Arm: | 14.7 Cm | Pages 194–195 |
| Abdominal Press: | 0.00 N/Cm 2 | Page 196 |
| Abdominal Force: | 5.9 N | Page 197 |
| Erector Spinae Muscle Force: | 4085.5 N | Page 197 |
| Rectus Abdominus Muscle Force: | 0.0 N | Page 197 |

TABLE 1-continued

Ergometrics Biomechanical Model

| | | |
|---|---|---|
| Lumbodorso Fascia Strain: | 0.0% | Page 197 |
| L5/S1 Compression: | 4229.2 N | Page 199 |

Both screen displays may be printed for a permanent record as indicated at block 76.

Block 78 denotes identification of the weakest link (Hip in example) and calculation of the expected limit for the weakest link equal to 75% by increasing or decreasing the exertion to obtain the 75%. If rotation is involved enter the degree of rotation and adjust expected limit by 10%, 15% or 30% for 30°, 60° or 90° rotation respectively.

Figure 5:
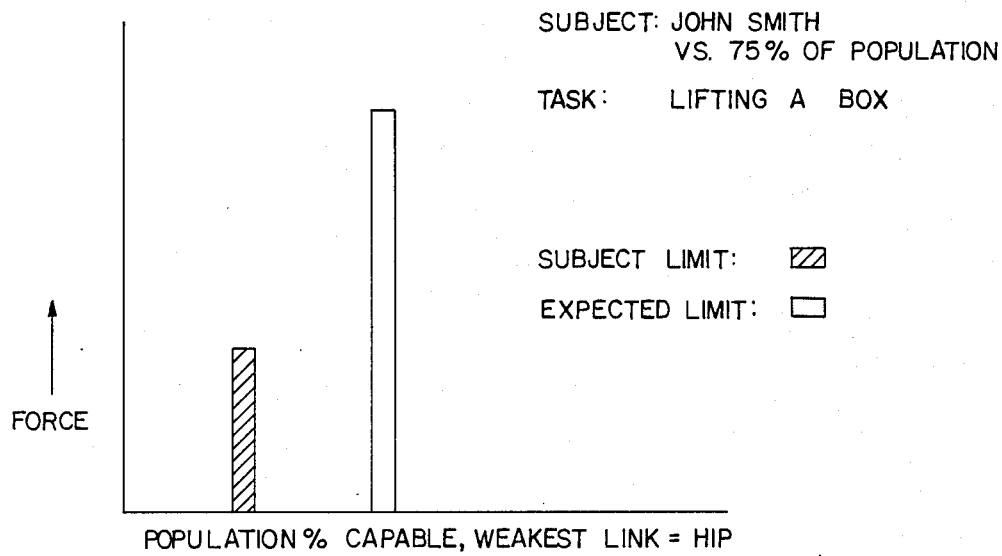
FIG. 5 is a subject comparison chart.

Block 80 denotes comparison of the subject's expected limit to the subject's exertion which is then screen displayed graphically as indicated by Block 82 and in written format by Block 84. Examples are illustrated by FIG. 5 and the following format:

| | |
|---|---|
| Date: | 9-12-86 |
| Task #: | 1 |
| Description: | LIFTING A BOX |
| Task #1 involved an isometric lift, vertical (V) 15 inches from the floor and horizontal (H) 12 inches from the midline of the body. The subject was able to exert a force that would be equal to lifting and holding 30 lbs. in this posture. | |
| Subjects exertion: | 30 lbs. |
| Expected limit: | 78 lbs. |
| Weakest link: | Hip |
| Score: | 38% |

Block 86 denotes printing of the screen displays in Blocks 82 and 84.

Block 88 denotes the summary of the three repeated tasks in terms of task number, exertion and expected limit.

A final composite summary is denoted by Block 90 and calculated as follows:
A. The exertions are averaged.
B. The expected limits are averaged.
C. The average exertions are divided by the average expected limit.
D. The percent strength impairment is calculated:
　1. If average exertions are greater than average expected limits then no apparent impairment.
　2. Otherwise subtract the percentage result from "C" from 95% to determine the strength impairment.
E. The percentage result from "C" is multiplied by 35 lbs. and 20 lbs. to calculate male and female weight restrictions.

Block 92 denotes screen display and Block 94 printing of the summary as shown in the following example format:

| Summary |
|---|
| A.　Total Exertions 155 Lbs./Number of Tasks 5 = 31 |
| B.　Total Expected Limits 388 Lbs./Number of Tasks 5 = 78 |
| C.　Score (A/B) = 39.95% |
| D.　Percent of Strength Impairment = 55.05% |
| E.　Weight Restriction = 14 Lbs. for Males 8 Lbs. for Females |

As an option the philosophy of the biomechanical model employed and the isometric strength testing unit may be printed as an attachment to the printouts above. The software employed has been written in Turbo Pascal for the disability evaluation and employed on an IBM PC 2 Model 30 with an Epson Model EX 800 printer.

Figure 6:
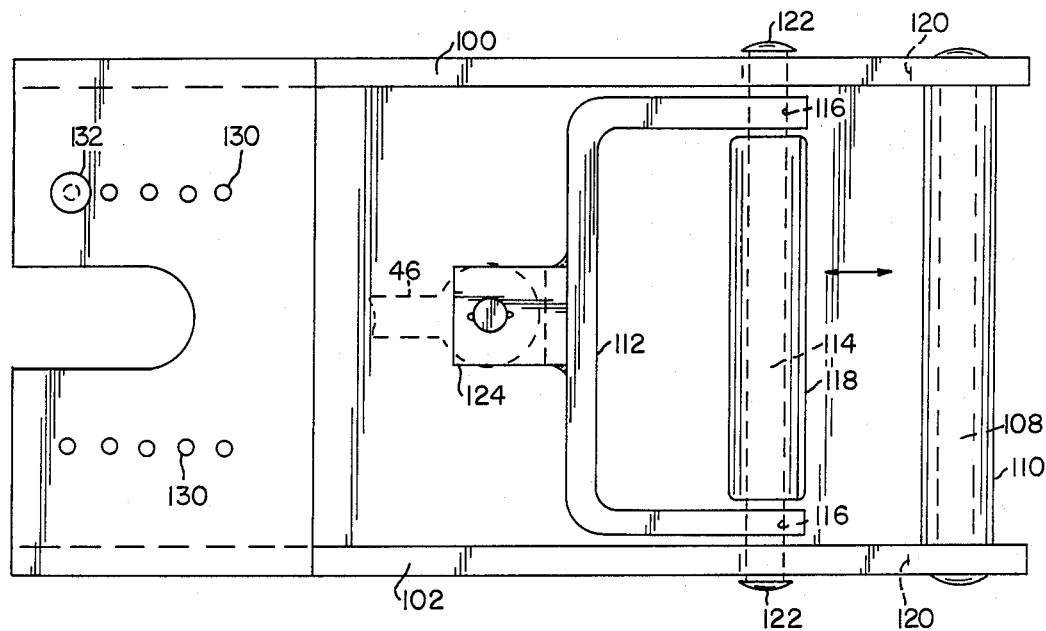
FIG. 6 is a side view of the new squeeze grip attachment.
Figure 7:
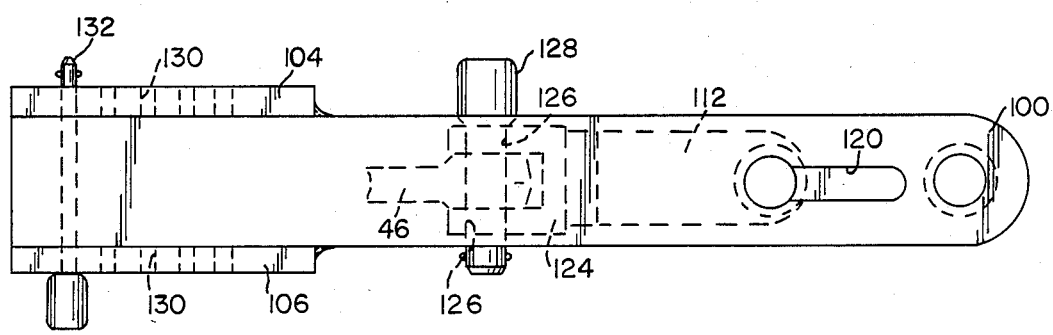
FIG. 7 is a top view of the new squeeze grip attachment.

In FIGS. 6 and 7 the new squeeze grip attachment is illustrated. The new squeeze grip comprises upper 100 and lower 102 frame members and a pair of side plates 104 and 106 that join the frame members together permanently. At the opposite end of the attachment is a frame bar 108 permanently joining the upper 100 and lower 102 frame members together. Frame bar 108 is covered with a relatively soft foam grip material 110.

Between the upper 100 and lower 102 frame members is a movable handle 112 having a handle bar 114 extending vertically through holes 116 in the bifurcated end of the handle. The handle bar 114 is also covered with a soft foam grip material 118 between the bifurcated ends. Beyond the holes 116 the handle bar 114 extends through a pair of slots 120 in the upper 100 and lower 102 frame members. Fasteners 122 assure that the handle bar 114 remains properly positioned as it is slid toward and away from the frame bar 108.

At the center of the handle 112 is a bifurcated bracket 124 bored horizontally 126 to accept a removable pin 128 for attachment to the eye-bolt 46 and load cell 42 of the horizontal arm 28 (see FIG. 1). Side plates 104 and 106 include a plurality of horizontally aligned sets of holes 130. Removable pins 132 selectably engage the holes 130 and matching holes 134 in the head 40 above and below the head pivot point 44. The particular set of holes 130 selected determine the neutral or unloaded position of the handle 112 and handle bar 114. Thus, the squeeze grip can be adjusted for hand size. In combination with the vertical post assembly and complete unit shown in FIG. 1, the squeeze grip can be set at the proper elevation. The sliding motion of the squeeze grip provides a pure measure of tension on the load cell 42 without torque thus, the hand may be right side up or upside down in placement on the grip.

Figure 8:
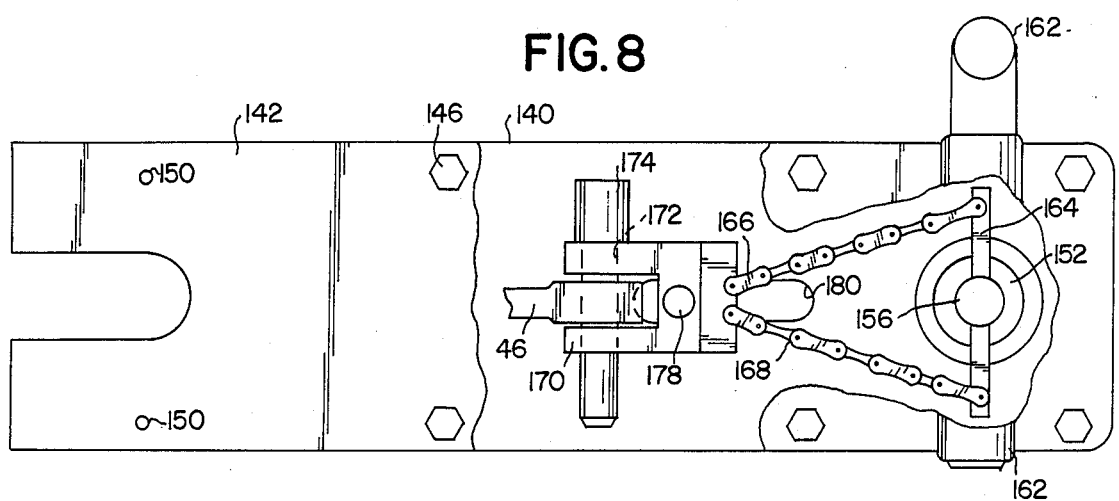
FIG. 8 is a side view of the torque testing attachment.
Figure 9:
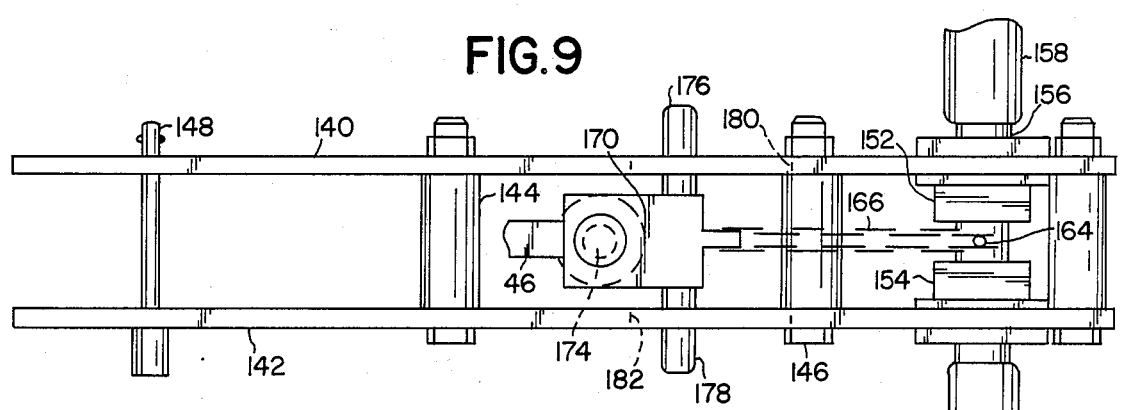
FIG. 9 is a top view of the torque testing attachment.
Figure 10:
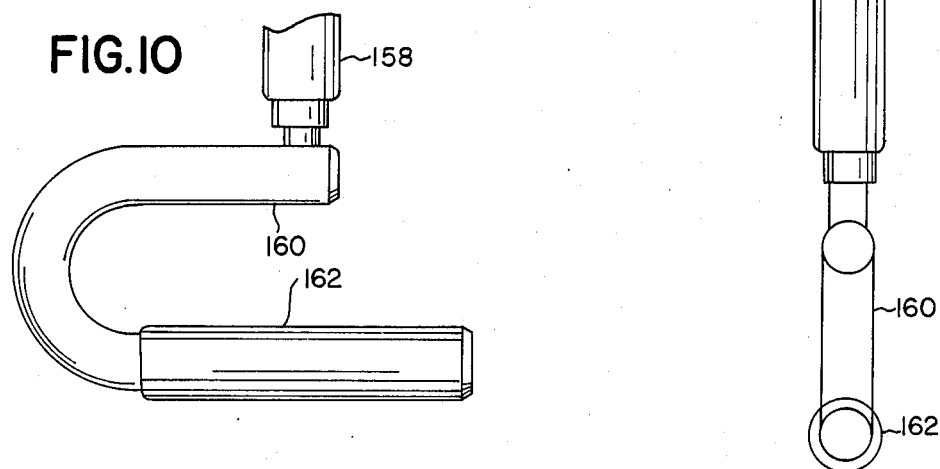
FIG. 10 is a detail of the torque testing attachment.

In FIGS. 8, 9 and 10 the torque testing unit is illustrated. A pair of side plates 140 and 142 are fastened together with spacers 144 and bolts 146. The side plates attach with a pin 148 through holes 150 in the side plates to the head 40 on the arm 28. At the outboard end of the side plates 140 and 142 are a pair of bearings 152 and 154 mounted in the side plates. A rotatable shaft 156 extends through the bearings 152 and 154 and is covered on each side with grip material 158. Attached to one end of the shaft 156 is a U-shaped rod 160 having a portion covered with grip material 162.

Between the bearings 152 and 154 a vertical rod 164 extends above and below the shaft 156 and is attached to the shaft. At the top and bottom of the rod 164 short lengths of chain 166 and 168 are attached. The chains 166 and 168 extend and attach to a bifurcated block 170. The bifurcated block 170 includes a bore 172 through the bifurcated end for a pin 174 attachment to the eye-bolt 46 and load cell 42. Extending horizontally from either side of the block 170 are pins 176 and 178 which engage slots 180 and 182 in the side plates 140 and 142.

Gripping and turning the U-shaped rod 160 provides a test of pronation/supination torque with the forearm parallel to shaft 156. Gripping and turning the U-shaped rod 160 with the forearm perpendicular to the shaft 156 provides a test of ulnar/radial deviation torque. Gripping and turning the shaft 156 provides a test of flexion/extension torque. Thus, all three rotations of the hand can be tested with the torque testing unit at the proper height on the arm 28 and vertical assembly 20. The proper height for the subject person depends upon individual height and desired arm orientation. For example, the subject's arm may be fully extended or the upper arm vertical and lower arm extended.

I claim:

1. In an isometric strength testing system which includes a disability analysis computer program, an isometric strength test unit comprising a vertical column and a horizontal arm of the vertical column, a load sensor on the arm and grip means on the arm connected to the load sensor to enable a subject person to apply an isometric load to the load sensor, means to electrically monitor the load sensor as a function of time and means to record the load applied to the load sensor as a function of time, the steps of,
- having an unrestrained subject person apply an isometric load at least one time to the grip means on the arm,
- photographing the subject person during the application of the load to the arm,
- entering the subject person's height, weight, and sex into the program, digitizing the photograph to measure body angles and entering the measurements into the program,
- in the program calculating the subject person's anthropometric data including body link lengths, centers of gravity and weights from the subject person's height, weight, sex and digitized body angles,
- into the program entering the subject person's actual load exerted, direction of exertion and number of hands from the application of the isometric load to the grip means,
- in the program calculating the subject person's joint compression expressed as a population percentage capability at each selected joint from the calculated anthropometric data, direction of exertion, number of hands and actual load exerted,
- in the program reiteratively recalculating the joint compression at each selected joint by repeatedly adjusting the value of load exerted until the value of joint compression at one of the joints substantially equals a predetermined value expressed as a specified percentage of population capability to thereby determine an expected load exerted, and
- comparing the subject person's expected load exerted to the subject person's actual load exerted.

2. The strength testing system of claim 1 including the steps of,
- averaging the actual loads exerted over the number of tests,
- averaging the expected loads exerted over the number of tests,
- dividing the averaged actual loads exerted by the average expected loads exerted and,
- if less than 0.95, multiplying by 100 to obtain a result,
- subtracting the result from 95% to determine strength impairment, and
- multiplying the result by specified weights to determine male and female weight restrictions for the subject person, and
- if greater than 0.95, then indicating no impairment.

3. The strength testing system of claim 2 wherein the specified weights for male and female are respectively 35 lbs. and 20 lbs.

4. The strength testing system of claim 1 wherein the specified percentage of the population capability is 75%.

5. The strength testing system of claim 1 including the steps of,
- averaging the actual loads exerted over the number of tests,
- averaging the expected loads exerted over the number of tests,
- dividing the averaged actual loads exerted by the average expected loads exerted and,
- if less than a specified value, subtracting from the specified value and multiplying by 100 to determine percentage strength impairment.

6. An isometric strength testing apparatus comprising an isometric strength test unit having a vertical column and a horizontal arm on the vertical column, a load sensor on the arm and grip means on the arm connected to the load sensor to enable a subject person to apply an isometric load to the load sensor, means to electrically monitor the load sensor as a function of time and means to record the load applied to the load sensor as a function of time, and
- a disability analysis computer including a program comprising:
- means to input anthropometric data from published human surveys and a subject person's height, weight, and sex to the computer,
- means to digitize a subject person's unrestrained testing configuration and enter the digitized configuration information including body angles, direction of exertion and number of hands into the computer,
- means to input a subject person's actual load exerted from the application of the isometric load,
- means to calculate the subject person's anthropometric data including body link lengths, centers of gravity and weights from the subject person's height, weight, sex and digitized body angles,
- means to calculate the subject person's joint compression expressed as a population percentage capability at each selected joint from the calculated anthropometric data, direction of exertion, number of hands and actual load exerted,
- means to reiteratively recalculate the joint compression at each selected joint by repeatedly adjusting the value of load exerted until the value of joint compression at one of the joints substantially equals a predetermined value expressed as a specified percentage of population capability to thereby determine an expected load exerted, and
- means to compare the subject person's expected load exerted (limit) to the subject person's actual load exerted.

7. The isometric strength testing apparatus of claim 6 including the additional means to:
- average the actual loads exerted over a number of tests,
- average the expected loads exerted over the number of tests,
- divide the averaged actual loads exerted by the average expected loads exerted and,
- if less than 0.95, multiply by 100 to obtain a result,
- subtract the result from 95% to determine strength impairment, and multiply the result by specified weights to determine male and female weight restrictions for the subject person.

8. The isometric strength testing apparatus of claim 7 wherein the specified weights for male and female are respectively 35 lbs. and 20 lbs.

9. The isometric strength testing apparatus of claim 6 wherein the specified percentage of the population capability is 75%.

10. The isometric strength testing apparatus of claim 6 including additional means to:
average the actual loads exerted over a number of tests,
average the expected loads exerted over the number of tests,
divide the averaged actual loads exerted by the averaged expected loads exerted and,
if less than a specified value, subtract from the specified value and multiply by 100 to determine percentage strength impairment.

11. In a disability analysis isometric strength testing system which includes a computer program, an isometric strength testing unit comprising means to support a load sensor, a load sensor on the support means and grip means on the support means connected to the load sensor to enable a subject person to apply an isometric load to the load sensor, means to monitor the load sensor as a function of time and means to record the load applied to the load sensor as a function of time, the steps of, p1 measuring and recording a subject person's height, weight, and sex,
having an unrestrained subject person apply an isometric load to the grip means,
measuring and recording the subject person's actual load exerted, direction of exertion and number of hands from the application of the isometric load,
photographing the subject person during application of the load and digitizing the photograph to measure and record body angles,
calculating the subject person's anthropometric data including body link lengths, centers of gravity and weight from the subject person's height, weight, sex and digitized body angles,
calculating the joint compression for several selected joints of the subject person from the calculated anthropometric data, direction of exertion, number of hands, sex and actual load exerted,
reiteratively recalculating the joint compression at each selected joint by repeatedly adjusting the value of load exerted until the value of joint compression at one of the joints substantially equals a predetermined value to thereby determine an expected load exerted, and
comparing the subject person's expected load exerted to the subject person's actual load exerted to determine the subject person's disability.

12. An isometric strength testing apparatus comprising means to support a load sensor, a load sensor on the support means and grip means on the support means connected to the load sensor to enable a subject person to apply an isometric load to the load sensor, means to monitor the load sensor as a function of time and means to record the load applied to the load sensor as a function of time, means to record and digitize the posture of an unrestrained subject person during loading of the sensor, said means to record and digitize providing measurements of body angles, direction of exertion and number of hands of the subject person during isometric loading of the sensor, and
computer means to calculate the expected load exerted by the subject person and compare with the subject person's actual load exerted to determine the subject person's disability, said means to calculate including means to input the subject person's height, weight, and sex for the calculation of anthropometric data including body link lengths, centers of gravity and weight, and means to input the actual load exerted, the body angles, direction of exertion and number of hands for the calculation of joint compression at several selected joints of the subject person, and
means to reiteratively recalculate the joint compression at each selected joint by repeatedly adjusting the value of load exerted until the value of joint compression at one of the selected joints substantially equals a predetermined value to thereby determine an expected load exerted for comparison with the actual load exerted.

* * * * *

UNITED STATES PATENT AND TRADEMARK OFFICE
CERTIFICATE OF CORRECTION

PATENT NO. : 4,882,677
DATED : November 21, 1989
INVENTOR(S) : Thomas M. Curran

It is certified that error appears in the above-identified patent and that said Letters Patent is hereby corrected as shown below:

Column 5, lines 42- 62:

In TABLE I, under "Body Link" in the second, third and fourth subtables reverse the first column of each subtable to read vertically down:

-- Ankle
   Knee
   Hip
   L5/S1
   Shoulder
   Elbow --

Signed and Sealed this

Sixteenth Day of March, 1993

Attest:

STEPHEN G. KUNIN

Attesting Officer

Acting Commissioner of Patents and Trademarks